US008439837B2

(12) United States Patent
Noujaim et al.

(10) Patent No.: US 8,439,837 B2
(45) Date of Patent: May 14, 2013

(54) SYSTEMS AND METHODS FOR DETECTING HYPOGLYCEMIC EVENTS HAVING A REDUCED INCIDENCE OF FALSE ALARMS

(75) Inventors: Sharbel E. Noujaim, Menlo Park, CA (US); David Horwitz, Los Altos, CA (US); Manoj Sharma, Milpitas, CA (US); Joseph Marhoul, San Jose, CA (US)

(73) Assignee: LifeScan, Inc., Milpitas, CA (US)

( * ) Notice: Subject to any disclaimer, the term of this patent is extended or adjusted under 35 U.S.C. 154(b) by 1530 days.

(21) Appl. No.: 11/928,560

(22) Filed: Oct. 30, 2007

(65) Prior Publication Data
US 2008/0208026 A1 Aug. 28, 2008

Related U.S. Application Data

(60) Provisional application No. 60/863,660, filed on Oct. 31, 2006, provisional application No. 60/974,397, filed on Sep. 21, 2007.

(51) Int. Cl.
*A61B 51/14532* (2006.01)
*A61B 51/14503* (2006.01)

(52) U.S. Cl.
USPC .......................................... 600/365; 600/373

(58) Field of Classification Search ........................ None
See application file for complete search history.

(56) References Cited

U.S. PATENT DOCUMENTS

| | | | |
|---|---|---|---|
| 5,482,035 A | 1/1996 | Paloheimo | |
| 5,804,048 A | 9/1998 | Wong et al. | |
| 6,272,480 B1 | 8/2001 | Tresp et al. | |
| 6,348,274 B1 | 2/2002 | Kamiguchi et al. | |
| 6,526,298 B1* | 2/2003 | Khalil et al. | 600/310 |
| 6,574,490 B2 | 6/2003 | Abbink et al. | |
| 6,653,091 B1 | 11/2003 | Dunn et al. | |
| 6,882,940 B2 | 4/2005 | Potts et al. | |
| 6,923,763 B1 | 8/2005 | Kovatchev et al. | |
| 7,011,630 B2 | 3/2006 | Desai et al. | |
| 7,022,072 B2 | 4/2006 | Fox et al. | |
| 7,025,425 B2 | 4/2006 | Kovatchev et al. | |
| 7,261,691 B1* | 8/2007 | Asomani | 600/300 |
| 2003/0028089 A1 | 2/2003 | Galley et al. | |
| 2004/0248204 A1 | 12/2004 | Moerman | |
| 2005/0038332 A1* | 2/2005 | Saidara et al. | 600/347 |
| 2005/0197621 A1 | 9/2005 | Poulsen et al. | |
| 2005/0214892 A1 | 9/2005 | Kovatchev et al. | |
| 2005/0240356 A1 | 10/2005 | Staib et al. | |

FOREIGN PATENT DOCUMENTS
EP 1102194 A2 5/2001

OTHER PUBLICATIONS

Noujaim et al (Journal of Diabetes Science and Technology, Sep. 2007, vol. 1, pp. 652-668).*
Palerm C. C., et al., "Hypoglycemia Prediction and Detection Using Optimal Estimation" Symposium Paper—Diabetes Technology & Therapeutics vol. 7, No. 1, 2003: 3-14.
Bequette B. W., "Optimal Estimation Applications to Continuous Glucose Monitoring", In: Proceedings of the American Control Conference, Boston: IEEE, 2004: 958-962.
Klonoff D. C., "A Review of Continuous Glucose Monitoring Technology", Diabetes Technology & Therapeutics vol. 7, No. 5, 2005: 770-775.
Kollman C. et al, "Limitations of Statistical Measures of Error in Assessing the Accuracy of Continuous Glucose Sensors", Diabetes Technology & Therapeutics vol. 7, No. 5, 2005: 665-672.
Bode B. et al., "Alarms based on real time sensor glucose values to alert patients to hypo- and hyperglycemia: The Guardian continuous monitoring system", Diabetes Technology & Therapeutics vol. 6, 2004: 105-113.
Kovatchev B. P. et al., Evaluating the Accuracy of Continuous Glucose-Monitoring Sensors—Continuous glucose-error grid analysis illustrated by TheraSense Freestyle Navigator Data, Diabetes Care, vol. 27, No. 8, Aug. 2004: 1922-1928.
Wentholt I. M. et al., "A Critical Appraisal of the Continuous Glucose-Error Grid Analysis", Diabetes Care, vol. 28, No. 8, Aug. 2006: 1805-1811.
Hayter P. G., et al., "Performance Standards for Continuous Glucose Monitors", Diabetes Technology & Therapeutics vol. 7, No. 5, 2005: 721-726.
Briegel, Thomas, et al., "A Nonlinear State Space Model for the Blood Glucose Metabolism of a Diabetic", Anwendungsaufsatz, pp. 228-236, Automatisierungstechnik 50, May 2002, Oldenbourg Verlag.
Eddy, S.R. "What is a Hidden Markov Model?", Nature Biotechnology, pp. 1315-1316, vol. 22, No. 10, Oct. 2004.
Pentland, Alex, "Healthwear: Medical Technology Becomes Wearable", Computer, pp. 42-49, vol. 37, No. 5, May 2004.
Roweis, Sam "SCIA 2003 Tutorial: Hidden Markov Models", University of Toronto, 10 pages, Jun. 29, 2003.
Tresp, Volker, et al., "Neural-Network Models for the Blood Glucose Metabolism of a Diabetic", IEEE Transactions on Neural Networks, pp. 1204-1213, vol. 10, No. 5, Sep. 1999.

* cited by examiner

*Primary Examiner* — Karen Canella

(57) ABSTRACT

The present invention is directed to a method of reducing false readings in a hypoglycemic detector that includes establishing a predetermined hypoglycemic threshold, a predetermined critical threshold, a predetermined rate of change in glucose concentration where the predetermined critical threshold is below the predetermined hypoglycemic threshold. A first sampling rate is then calculated based upon said predetermined hypoglycemic threshold, said predetermined critical threshold, and said predetermined rate of change in glucose concentration.

6 Claims, 8 Drawing Sheets

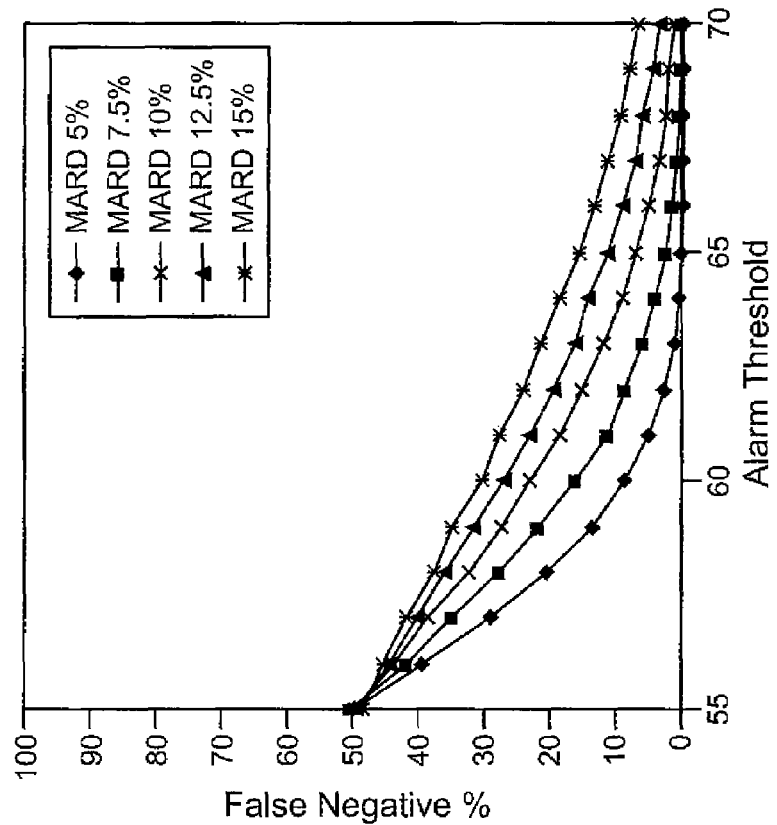
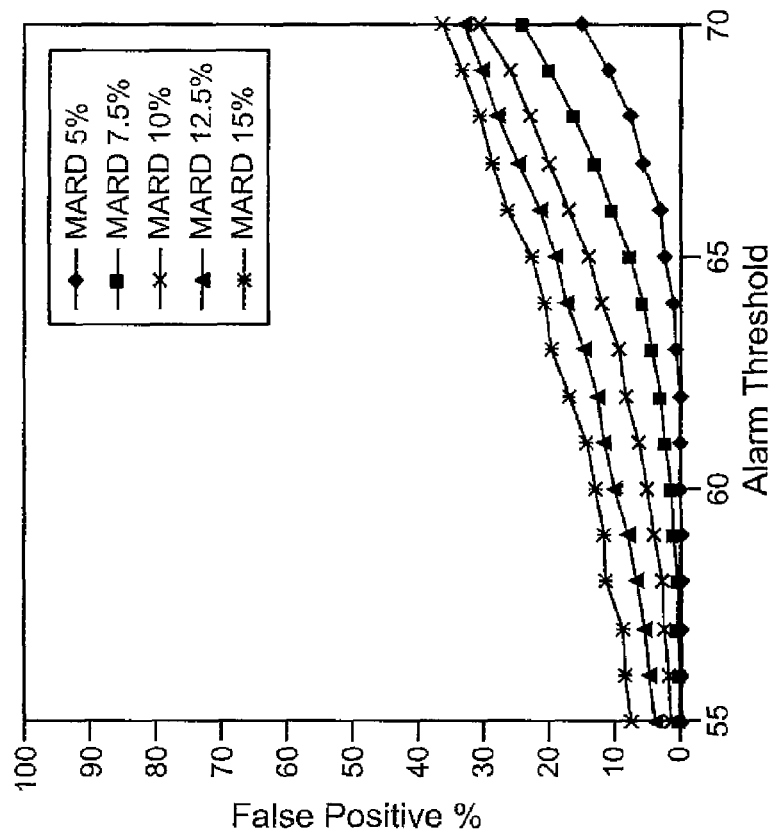

SYSTEMS AND METHODS FOR DETECTING HYPOGLYCEMIC EVENTS HAVING A REDUCED INCIDENCE OF FALSE ALARMS

This application claims the benefit of U.S. Provisional Application No. 60/863,660, filed Oct. 31, 2006 and U.S. Provisional Application No. 60/974,397, filed Sep. 21, 2007, which are incorporated herein by reference in their entirety.

The present invention is directed to an improved continuous glucose monitor and, more particularly, an improved method of reducing false readings in a hypoglycemic detector.

BACKGROUND OF THE INVENTION

A continuous glucose monitor (CGM) can measure several glucose concentrations over a period of time. Examples of CGM's can be an electrochemical sensor implanted in the subcutaneous layer, an ex vivo electrochemical sensor that measures extracted physiological fluid, or a non-invasive glucose sensor using reflected infrared light, as described in U.S. Pat. Nos. 6,348,274; 5,804,048; and 6,574,490. One of the potential benefits of a CGM is the ability to notify a person with diabetes of a hypoglycemic event. In general, a person with diabetes would like to reduce the incidence of hypoglycemia to mitigate the risk of incurring serious short-term harm (e.g., loss of consciousness, coma, and death) and long-term harm (e.g., cardiac disease, retinopathy, and kidney disease). A hypoglycemic alarm can potentially reduce the amount of time that a person with diabetes is in the hypoglycemic state because appropriate therapeutic action (e.g., consume glucose or reduce insulin intake) can be immediately initiated when the alarm is triggered.

SUMMARY

In a method for reducing false readings in a hypoglycemic detector in accordance with the present invention, the method may include establishing a predetermined hypoglycemic threshold $G_{hypo}$, a predetermined critical threshold $G_{crit}$, and a predetermined rate of change in glucose concentration bgr. It should be noted that the predetermined critical threshold $G_{crit}$ is below the predetermined hypoglycemic threshold $G_{hypo}$. Next, a first sampling rate is calculated based upon the predetermined hypoglycemic threshold $G_{hypo}$, the predetermined critical threshold $G_{crit}$, and the predetermined rate of change in glucose concentration bgr.

In a method for reducing false readings in a hypoglycemic detector in accordance with the present invention, as set forth above, the predetermined rate of change in glucose concentration bgr may be a negative rate of change in glucose concentration. In one embodiment, the negative rate of change in glucose concentration may be based upon a plurality of previously measured glucose concentrations of a user.

In a method for reducing false readings in a hypoglycemic detector in accordance with the present invention, as set forth above, the predetermined rate of change in glucose concentration bgr may be a maximum value of an absolute rate observed in people having diabetes to reduce the risk of having a false negative error if a user is experiencing a rapid drop in glucose concentration when the hypoglycemic alarm is activated.

In a method for reducing false readings in a hypoglycemic detector in accordance with the present invention, as set forth above, the method may further include measuring an actual rate of change in glucose concentration bĝr using the first sampling rate and modifying the first sampling rate based upon the actual rate of change in glucose concentration bĝr to give a second sampling rate. In one embodiment, the second sampling rate is less than the first sampling rate if the actual rate of change in glucose concentration bĝr is less than the predetermined rate of change in glucose concentration bgr.

In a method for reducing false readings in a hypoglycemic detector in accordance with the present invention, as set forth above, the step of establishing a first sampling rate may include the steps of multiplying a preferred number of measurements within a target zone TZ with the predetermined rate of change in glucose concentration bgr to give a product. Next, the product is divided by a difference between the predetermined critical threshold $G_{crit}$ and the predetermined hypoglycemic threshold $G_{hypo}$ to give the first sampling rate. In one embodiment, the preferred number of measurements within the target zone TZ may be about three.

In a method for reducing false readings in a hypoglycemic detector in accordance with the present invention, as set forth above, the preferred number of measurements within the target zone TZ may be a number of glucose measurements measured within a glucose concentration interval and within a time interval. The glucose concentration interval is from about the predetermined critical threshold $G_{crit}$ to about the predetermined hypoglycemic threshold $G_{hypo}$. The time interval is from a lower time value $t_{lower}$ where the continuous glucose monitor is estimated to measure a glucose concentration at the predetermined hypoglycemic threshold $G_{hypo}$ to an upper time value $t_{upper}$ where the continuous glucose monitor is estimated to measure a glucose concentration at the predetermined critical threshold $G_{crit}$.

In a method for establishing a critical sampling rate for a continuous glucose monitor in accordance with the present invention, the method may include establishing a preferred number of measurements within a target zone TZ, a predetermined critical threshold $G_{crit}$, and a predetermined hypoglycemic threshold $G_{hypo}$. Next, a plurality of glucose concentrations are measured at a predetermined first sampling rate. An actual rate of change in glucose concentration bĝr is calculated based on the plurality of glucose concentrations. The first sampling rate is modified to a second sampling rate using a function based on the preferred number of measurements within a target zone TZ, the predetermined critical threshold $G_{crit}$, the predetermined hypoglycemic threshold $G_{hypo}$, and the actual rate of change in glucose concentration bĝr. In one embodiment, a hypoglycemic alarm is activated to detect a hypoglycemic glucose concentration once the first sampling rate is modified to give a second sampling rate.

In a method for establishing a critical sampling rate for a continuous glucose monitor in accordance with the present invention, as set forth above, the step of modifying the first sampling rate to the second sampling rate may include multiplying the preferred number of measurements within a target zone TZ with the actual rate of change in glucose concentration bĝr to give a product. Next, the product is divided by a difference between the predetermined critical threshold $G_{crit}$ and the predetermined hypoglycemic threshold $G_{hypo}$ to give the second sampling rate. In accordance with the present invention, the preferred number of measurements within the target zone TZ may be about three. In accordance with the present invention, the predetermined critical threshold $G_{crit}$ may be about 55 mg/dL and the predetermined hypoglycemic threshold $G_{hypo}$ may be about 70 mg/dL. In accordance with the present invention, the actual rate of change in glucose concentration bĝr may range from about negative 5 milligram per deciliter per minute to about zero milligram per deciliter per minute.

In a method for establishing a critical sampling rate for a continuous glucose monitor in accordance with the present invention, as set forth above, the preferred number of measurements within the target zone TZ may be a number of glucose measurements within a glucose concentration interval and within a time interval. The glucose concentration interval is from about the predetermined critical threshold $G_{crit}$ to about the predetermined hypoglycemic threshold $G_{hypo}$. The time interval is from a lower time value $t_{lower}$ where the continuous glucose monitor is estimated to measure a glucose concentration at the predetermined hypoglycemic threshold $G_{hypo}$ to an upper time value $t_{upper}$ where the continuous glucose monitor is estimated to measure a glucose concentration at the predetermined critical threshold $G_{crit}$.

In an embodiment in accordance with the present invention, a continuous glucose monitor may include a sensor portion, a memory, and a microprocessor. The sensor portion may be configured to measure a plurality of glucose concentrations over a period of time. The memory may be configured to save the plurality of glucose concentrations, a hypoglycemic threshold $G_{hypo}$, and a critical threshold $G_{crit}$. The microprocessor may be configured to calculate an actual rate of change in glucose concentration per unit time bĝr based on the plurality of glucose concentrations, and calculate a sampling rate based upon the hypoglycemic threshold $G_{hypo}$, the critical threshold $G_{crit}$, and the actual rate of change in glucose concentration per unit time bĝr.

In an embodiment in accordance with the present invention, as set forth above, a continuous glucose monitor may include a microprocessor that is also configured to calculate whether a measured glucose concentration is within a target zone. The target zone may include a glucose concentration interval and a time interval. The glucose concentration interval is from about the predetermined critical threshold $G_{crit}$ to about the predetermined hypoglycemic threshold $G_{hypo}$. The time interval is from a lower time value $t_{lower}$ where the continuous glucose monitor is estimated to measure a glucose concentration at the predetermined hypoglycemic threshold $G_{hypo}$ to an upper time value $t_{upper}$ where the continuous glucose monitor is estimated to measure a glucose concentration at the predetermined critical threshold $G_{crit}$.

In an embodiment in accordance with the present invention, as set forth above, a continuous glucose monitor may include a microprocessor that is also configured to calculate a product by multiplying a preferred number of measurements within a target zone TZ with the actual rate of change in glucose concentration bĝr. The microprocessor is also configured to calculate the sampling rate by dividing the product by a difference between the predetermined critical threshold $G_{crit}$ and the predetermined hypoglycemic threshold $G_{hypo}$.

In an embodiment in accordance with the present invention, as set forth above, a continuous glucose monitor may further include an alarm configured to alert a user that the continuous glucose monitor measured a hypoglycemic glucose concentration that was within the target zone.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A and 3B are graphs showing the incidence of false positive and false negative errors, respectively, when the alarm threshold is varied between 55 mg/dL and 70 mg/dL glucose concentration with a rate of change in glucose concentration per unit time of −1 mg/dL/min and a sampling rate of 0.2 samples per minute;

DETAILED DESCRIPTION OF ILLUSTRATIVE EMBODIMENTS OF THE INVENTION

Figure 1:
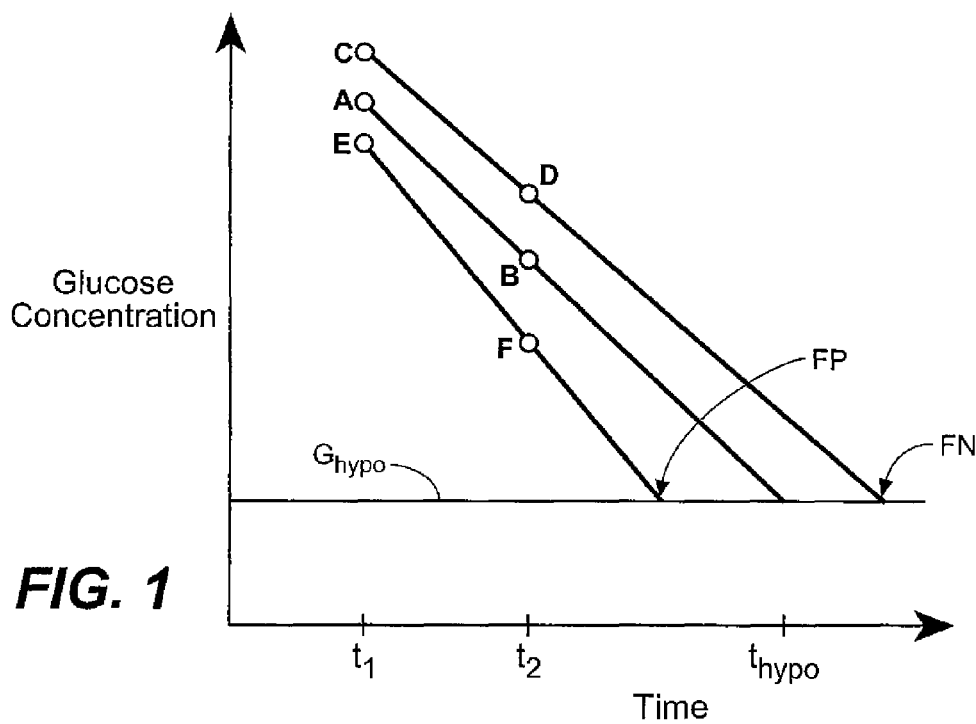
FIG. 1 is a chart illustrating glucose concentrations measured with a continuous glucose monitor (CGM) that has a negative bias (line EF), no bias (line AB), and a positive bias (line CD) with regards to a hypoglycemic threshold.

The following detailed description should be read with reference to the drawings, in which like elements in different drawings are identically numbered. The drawings, which are not necessarily to scale, depict selected exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

A CGM can be used to observe trends in measured glucose concentrations for helping people with diabetes manage their disease. In particular, monitoring a downward trend in glucose concentration can be especially noteworthy for identifying the onset of hypoglycemia. Once a downward trend in glucose concentration has been identified, a method for providing a hypoglycemic alarm can be implemented for alerting a user when the glucose concentration is below a pre-determined threshold such as, for example, 70 mg/dL.

Applicant believes that one of the challenges in providing a hypoglycemic alarm is ensuring that the percentage of false alarms is sufficiently low. More particularly, a false alarm can represent a false positive alarm or a false negative alarm or a combination thereof. A false positive alarm occurs when a hypoglycemic alarm is incorrectly triggered when a user's glucose concentration is euglycemic. A false negative alarm occurs when a hypoglycemic alarm is not triggered when a user's glucose concentration is in fact hypoglycemic. If the occurrence of false positive alarms becomes relatively high, a user may lose confidence in relying on the hypoglycemic alarm and stop using it. In addition, a false positive alarm can cause a user to unnecessarily increase their glucose concentration and, in a worse case scenario, cause a user in the euglycemic state to become hyperglycemic. A relatively high occurrence of false negative alarms can be potentially dangerous because a user can be unaware of his or her hypoglycemic state and not take the appropriate therapeutic action. In summary, a hypoglycemic alarm system that uses a CGM needs to have a sufficiently low percentage of false positive and false negative errors so that a user will have confidence in relying on the alarm, have the ability to take effective therapeutic action based on the alarm, and mitigate the risk of causing physiological harm due to an incorrect therapeutic action or lack thereof.

FIG. 1 is a chart illustrating a glucose concentrations measured with a CGM over time that has a negative bias (line EF), no bias (line AB), and a positive bias (line CD) with regards to a hypoglycemic threshold $G_{hypo}$. The CGM can alert a user of a hypoglycemic event when a measured glucose concentration along line AB intersects or is less than the hypoglycemic threshold $G_{hypo}$. In one embodiment, the hypoglycemic threshold $G_{hypo}$ may be about 70 mg/dL. The hypoglycemic threshold $G_{hypo}$ should not be limited to 70 mg/dL and could be assigned another glucose concentration known to be representative of hypoglycemia by a person skilled in the art. Under some circumstances, a CGM can have an error in identifying hypoglycemia because of one or more of the following factors such as, for example, CGM inaccuracy, imprecision, and sampling rate. The present invention will describe a hypoglycemic alarm that accounts for the aforementioned factors so that the false positive and false negative error rates are decreased.

A series of terms will be described in the immediately following section that is required for illustrating an embodiment of a hypoglycemic alarm in accord with the present invention. A hypoglycemic alarm can be described in terms of a time $t_{hypo}$ where the glucose concentration has just become hypoglycemic, as illustrated in FIG. 1. The term $t_{hypo}$ represents an amount of elapsed time from an initial time point $t_1$ to the onset of the hypoglycemic event. Equation 1 shows that $t_{hypo}$ can be calculated based on a hypoglycemic threshold $G_{hypo}$, an initial glucose concentration $G(t_1)$, and a rate of change in glucose concentration per unit time bgr.

$$t_{hypo} = \frac{G_{hypo} - G(t_1)}{bgr} \quad \text{Eq. 1}$$

The term bgr is represented in Equation 2.

$$bgr = \frac{G(t_2) - G(t_1)}{t_2 - t_1} = \frac{G(t_2) - G(t_1)}{\Delta t} \quad \text{Eq. 2}$$

The term $G(t_2)$ is a glucose concentration at time $t_2$ that is subsequent to time $t_1$.

As mentioned earlier, an inaccurate CGM measurement can affect the accuracy of a hypoglycemic alarm, which in turn, affects the identification of $t_{hypo}$. A glucose measurement $\hat{G}(t_n)$ can be inaccurate because it includes bias and noise, as defined in Equation 3.

$$\hat{G}(t_n) = G(t_n) + \% \, b \times G(t_n) + \% \, cv \times G(t_n) \times \epsilon_n \quad \text{Eq. 3}$$

The terms $G(t_n)$ is a true glucose concentration, % b is a bias relative to the true glucose concentration, % cv is a coefficient of variation due to noise in the glucose concentration measurement, and $\epsilon_n$ is an independent standard normal random variable. It should be noted that an error due to precision could be improved by increasing the number of glucose concentration measurements when calculating an average whereas an error due to bias cannot be improved by increasing the number of measurements.

A measured rate of change of blood glucose concentration $\hat{bgr}$ can be estimated by performing a linear regression on a plurality of blood glucose concentration measurements $(t_1, G(t_1)), \ldots, (t_n, G(t_n))$. Alternatively, $\hat{bgr}$ can be estimated by combining Equation 2 and 3 together to give Equation 4 as shown below.

$$\hat{bgr} = bgr + b \, \% \times bgr + \% \, cv \times E \quad \text{Eq. 4}$$

The term E is a normally distributed error with mean of zero and a variance depending on the plurality of blood glucose concentration measurements $(t_1, G(t_1)), \ldots, (t_n, G(t_n))$. It should be noted that an error due to precision can be improved by increasing the number of glucose concentration measurements when calculating a slope, or in this case $\hat{bgr}$, whereas an error due to bias cannot be improved by increasing the number of glucose measurements.

From Equations 3 and 4, it can be seen that for a non-ideal sensor the start up or initial conditions at time $t_1$ will differ from A (points C or E) and the rate of changes will be different along line CD or line EF. The actual $\hat{t}_{hypo}$ can be written as Equation 5.

$$\hat{t}_{hypo} = \frac{G_{hypo} - \hat{G}(t_1)}{bg\hat{r}} \quad \text{Eq. 5}$$

A line CD is an example of a CGM that is measuring glucose concentrations having a positive bias, as illustrated in FIG. 1. As a result of the positive bias, the actual $\hat{t}_{hypo}$ for the line CD is greater than the true $t_{hypo}$, which causes the user to be alerted to the hypoglycemic event after it had already occurred. Such a false negative (FN) result causes a user to remain hypoglycemic for a particular time interval where the user is not taking therapeutic action.

A line EF is an example of a CGM that is measuring glucose concentrations having a negative bias, as illustrated in FIG. 1. As a result of the negative bias, the actual $\hat{t}_{hypo}$ for the line EF is less than the true $t_{hypo}$, which causes the user to be alerted to the hypoglycemic event before it actually occurs. Such a false positive (FP) result could cause a user to immediately take therapeutic action when it is not needed.

From FIG. 1, it can be seen that the percentage of false positive alarms and false negative alarms can be influenced depending on the systematic bias % b and the coefficient of variation % cv. In FIG. 1, $t_{hypo}$ is essentially represented as a single discrete point in time. Thus, a CGM having a % b of zero and a modest % cv will have a false positive alarm rate of about 50% and a false negative alarm rate of about 50%. Because $t_{hypo}$ is a single time point and not a time interval, a modest amount of noise or bias would likely cause the glucose measurements to not intersect the hypoglycemic threshold $G_{hypo}$ at exactly $t_{hypo}$ resulting in a false positive or false negative error.

Figure 2:
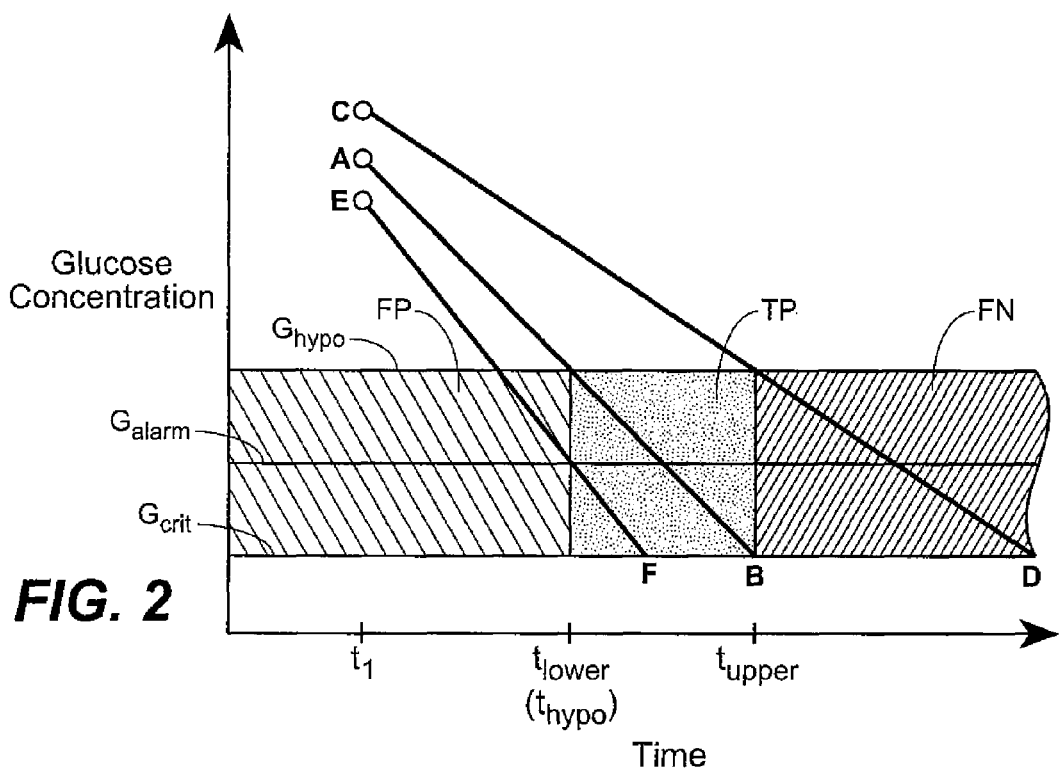
FIG. 2 is a glucose trending chart that includes a hypoglycemic threshold $G_{hypo}$, an alarm threshold $G_{alarm}$, and a critical threshold $G_{crit}$ for providing a hypoglycemic alarm in accordance with the present invention.

In a method of providing a robust hypoglycemic alarm that has a relatively low amount of false positive and false negative errors in accordance with the present invention, a true positive zone was created that includes a range of time values from $t_{lower}$ to $t_{upper}$, as illustrated in FIG. 2. It should be noted that the $t_{lower}$ in FIG. 2 is equivalent in time to $t_{hypo}$ in FIG. 1. The glucose trending graph of FIG. 2 includes three threshold values, which are a hypoglycemic threshold $G_{hypo}$, an alarm threshold $G_{alarm}$, and a critical threshold $G_{crit}$. The glucose trending graph of FIG. 2 also includes three zones, which are a false positive zone FP, a true positive zone TP, and a false negative zone FN. Note that the true positive zone may also be referred to as a target area or target zone. In FIG. 2, the true positive zone TP is essentially a rectangular box that is bounded by $t_{lower}$, $t_{upper}$, $G_{hypo}$, and $G_{crit}$.

The terms $t_{lower}$ to $t_{upper}$ are defined in Equations 6 and 7, respectively. A triggering of a hypoglycemic alarm at any time between $t_{lower}$ and $t_{upper}$ is classified as a true positive alarm.

$$t_{lower} = t_{hypo} = \frac{G_{hypo} - G(t_1)}{bgr} \quad \text{Eq. 6}$$

$$t_{upper} = \frac{G_{crit} - G(t_1)}{bgr} \quad \text{Eq. 7}$$

The term critical threshold $G_{crit}$ is a critical hypoglycemic threshold that represents a glucose concentration that is less than the hypoglycemic threshold $G_{hypo}$ in which a user should stop all activity so that immediate therapeutic action can be performed because there is a risk of a loss of consciousness and possibility of death. In one embodiment, the critical threshold $G_{crit}$ may be about 55 mg/dL. The critical threshold $G_{crit}$ should not be limited to 55 mg/dL and could be assigned another glucose concentration known to be representative of critical hypoglycemia to a person skilled in the art. The term $t_{upper}$ represents a time in which a glucose concentration measured with a CGM having a zero % b (line AB) intersects with the critical hypoglycemic threshold $G_{crit}$, as illustrated in FIG. 2.

A hypoglycemic alarm that occurs prior to $t_{lower}$ is a false positive error, which is indicated by line EF that intersects a false positive zone (FP), as illustrated in FIG. 2. The incidence of false positive errors for the system is defined by Equation 8. Note that a hypoglycemic event may be referred to as a "hypo event."

$$\text{False Positive \%} = \frac{\text{Number of patients who alarm before ``Target Area''}}{\text{Total number of patients with Hypo event}} \quad \text{Eq. 8}$$

A hypoglycemic alarm that occurs subsequent to $t_{upper}$ is a false negative error, which would be indicated by a line that intersects the false negative zone (FN). An example of a line that would intersect the false negative zone would be a line having a positive bias greater than the line CD. The incidence of false negative errors for the system is defined by Equation 9.

$$\text{False Negative \%} = \frac{\text{Number of patients who alarm after ``Target Area''}}{\text{Total number of patients with Hypo event}} \quad \text{Eq. 9}$$

A hypoglycemic alarm that occurs between $t_{lower}$ and $t_{upper}$ would be a line that intersects the true positive zone (TP). The incidence of true positive identification for the system is defined by Equation 10. Line AB and Line CD are examples of lines that intersect a boundary portion of the true positive zone. Although line CD has a positive bias, it is sufficiently small so that the CGM can still provide a true positive alarm. In summary, creating a true positive zone that is bounded by the range $t_{lower}$ and $t_{upper}$ allows the false negative alarm rate to decrease because a line having a positive bias such as line CD can still intersect a portion of a true positive zone (TP) as illustrated in FIG. 2.

$$\text{True Positive \%} = \frac{\text{Number of patients who alarm within ``Target Area''}}{\text{Total number of patients with Hypo event}} \quad \text{Eq. 10}$$

Another factor that can affect the false positive and false negative error rate for a hypoglycemic alarm is the sampling rate used by the CGM. If the sampling rate is sufficiently low, a false negative error could occur because a glucose concentration was not acquired in the target area. If the sampling rate is relatively high (>>critical sampling rate), the incidence of false positive errors would increase because the likelihood of identifying a single glucose measurement in the false positive zone increases. For instance, if a CGM outputs a relatively small number of glucose measurements that are in the false positive zone, the hypoglycemic alarm would likely identify those measurements if the sampling rate is sufficiently high. In one embodiment, a CGM may have a sufficiently high sampling rate so that one or more glucose measurements would occur within the target area for triggering a true positive hypoglycemic alarm. Based on the Nyquist-Shannon sampling theorem, it is known that to reconstruct an analog signal from discrete measurements, the sampling frequency must be at least twice that of the highest frequency contained in the signal. For monitoring physiological glucose concentrations, it is difficult to define such a frequency because the mean glucose value, the peak and low excursions around the mean and the maximum rate of change will vary from patient to patient. Therefore, for providing a robust hypoglycemic alarm with a relatively low false error rate, the sampling rate may be based on targeting a preferred number of measurements within the target area. A critical time interval $t_{critical}$ is defined in Equation 11 where the preferred number of measurements within the target area is about three.

$$t_{critical} = (t_{upper} - t_{lower})/3 \quad \text{Eq. 11}$$

Using the critical time interval $t_{critical}$, the sampling rate can be calculated using Equation 12.

$$\text{Critical Sampling Rate} \geq \frac{1}{t_{critical}} \quad \text{Eq. 12}$$

In an embodiment according to the present invention, a method for determining the critical sampling rate can be based upon an equation using the terms a preferred number of measurements within the target zone TZ, bgr, $G_{hypo}$, and $G_{crit}$. In one embodiment, Equation 13 can be used for determining the critical sampling rate. Equation 13 was derived by combining Equations 6, 7, 11, and 12 together. As a general trend, Equation 13 indicates that an increase in the absolute value of bgr will cause the critical sampling rate to increase and a decrease in the absolute value of bgr will cause the critical sampling rate to decrease, assuming that the % cv is constant.

$$\text{Critical Sampling Rate} \geq \frac{TZ * bgr}{G_{crit} - G_{hypo}} \quad \text{Eq. 13}$$

In an embodiment in accordance with the present invention, an initial critical sampling rate can be calculated using a maximum expected value of bgr when starting the hypoglycemic alarm. In this embodiment, a relatively high critical sampling rate will be used to mitigate the risk of a false negative alarm in case a user has a rapidly decreasing glucose concentration when the hypoglycemic alarm is initially activated. The maximum expected value of bgr can be based on historical glucose measurements of a user for a particular period of time or can be based on a maximum expected bgr for any user having diabetes. It should be noted that the invention should not be limited to using only a maximum expected value of bgr for a user and that other values for bgr can be used based on the circumstances.

In an embodiment in accordance with the present invention, a hypoglycemic alarm may initially use a first critical sampling rate that can then be modified to a second critical sampling rate based on an actual rate of change in glucose concentration bĝr. After a predetermined time interval, an actual rate of change in glucose concentration bĝr can be calculated using a plurality of glucose concentrations measured at a first critical sampling rate. The first sampling rate can then be modified at a predetermined time interval to account for changes in the actual rate of change in glucose concentration, which helps ensure that the sampling rate is at the critical sampling rate in Equation 13.

In an alternative embodiment in accordance with the present invention, a first sampling rate may be a predetermined value set by a user or be a factory default value. In this embodiment, the hypoglycemic alarm is not activated until a second sampling rate is implemented to ensure that a critical sampling rate is used. Using the first sampling rate, a plurality of glucose concentrations can be measured for a predetermined time interval. Next, an actual rate of change in glucose concentration bĝr can be calculated based on the plurality of glucose concentrations. The first sampling rate can then be modified to a second sampling rate based on the actual rate of change in glucose concentration bĝr using Equation 13. The hypoglycemic alarm can then be activated to detect a hypoglycemic glucose concentration once the first sampling rate is modified to the second sampling rate.

The preferred number of measurements within the target zone TZ can be a number of glucose measurements measured within a glucose concentration interval and within a time interval. The glucose concentration interval is from about the predetermined critical threshold $G_{crit}$ to about the predetermined hypoglycemic threshold $G_{hypo}$. The time interval is from a lower time value $t_{lower}$ where the continuous glucose monitor is estimated to measure a glucose concentration at the predetermined hypoglycemic threshold $G_{hypo}$ to an upper time value $t_{upper}$ where the continuous glucose monitor is estimated to measure a glucose concentration at the predetermined critical threshold $G_{crit}$.

Figure 12:
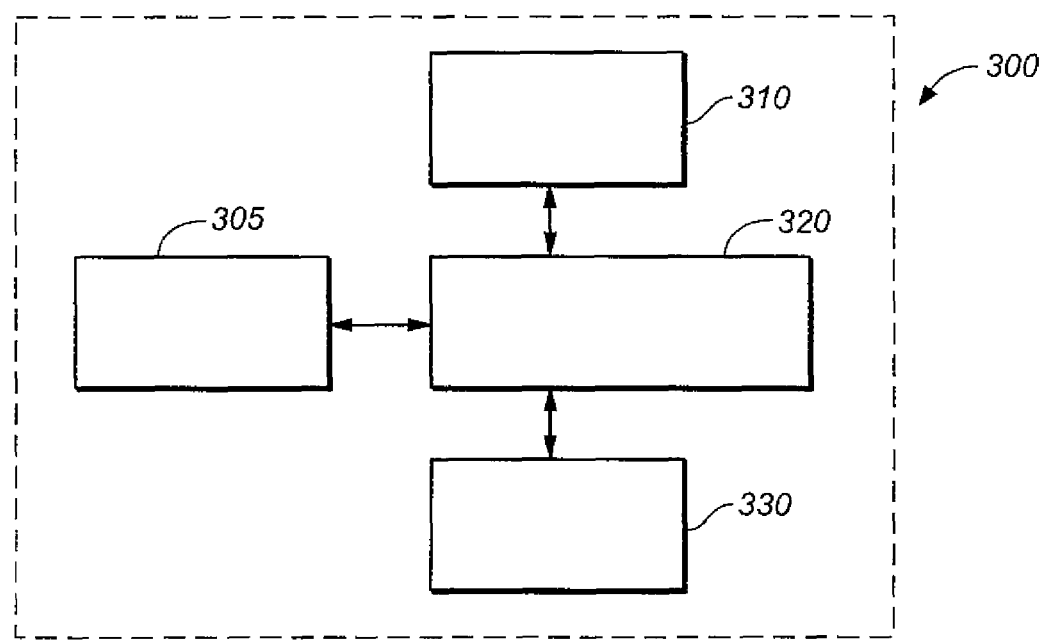
FIG. 12 is a simplified block diagram of a CCM for providing a hypoglycemic alarm according to an embodiment of the present invention.

FIG. 12 is a simplified block diagram of a CGM 300 (within the dashed lines) that provides a hypoglycemic alarm according to an embodiment of the present invention. CGM 300 can include a sensor portion 305, a memory 310, a microprocessor 320, and an alarm 330. The double-headed arrows of FIG. 12 indicate sensor portion 305, memory 310, microprocessor 320, and alarm 330 are all in operative communication with the each other be it by wired transmission, wireless transmission or other suitable means.

Memory 310 can be configured to receive and store a plurality of glucose concentrations as a function of time that were generated by CGM 300, hypoglycemic threshold $G_{hypo}$, critical threshold $G_{crit}$, a preferred number of measurement within a target zone TZ, a lower time value $t_{lower}$ and an upper time value $t_{upper}$. Memory 310 can be in the form of integrated circuits (e.g., DRAM and SRAM based memory modules) and/or optical memory technologies.

Microprocessor 320 can be configured to: (i) calculate an actual rate of change in glucose concentration per unit time based on the plurality of glucose concentrations; (ii) calculate a sampling rate based upon hypoglycemic threshold $G_{hypo}$, critical threshold $G_{crit}$, and the rate of change in glucose concentration per unit time bĝr; (iii) calculate whether a measured glucose concentration is within a target zone; and (iv) calculate a critical sampling rate using Equation 13.

Alarm 330 is configured to alert the user when a hypoglycemic glucose concentration is identified within the target zone. Alarm 330 can be, for example, a visual display, an audible alarm generation device, a tactile sensation generation device or any combination thereof.

In an embodiment of the present invention, a user can customize an alarm threshold $G_{alarm}$ that is lower than the hypoglycemic threshold $G_{hypo}$, but greater than the critical threshold $G_{crit}$, as illustrated in FIG. 2. Instead of triggering the alarm at the hypoglycemic threshold $G_{hypo}$, the alarm could be set for triggering when the measured glucose concentration becomes less than the alarm threshold $G_{alarm}$. For example, line EF intersects the alarm threshold $G_{alarm}$ at $t_{lower}$ causing the hypoglycemic alarm to be a true positive. Thus, selecting an alarm threshold that is less than the hypoglycemic threshold $G_{hypo}$, as illustrated in FIG. 2, can allow the incidence of false positive errors to decrease. However, an alarm threshold $G_{alarm}$ that is less than the hypoglycemic threshold $G_{hypo}$ can cause the incidence of false negative errors to increase. A user can opt to select a customizable alarm limit that is less than the hypoglycemic threshold for decreasing the incidence of false positive alarms, but at the same time, still provide an acceptable incidence of false negative alarms based on the personal preference of the user. In another embodiment, the alarm threshold $G_{alarm}$ can be defined to be any value greater than the critical threshold $G_{crit}$ that also includes a value greater than the hypoglycemic threshold $G_{hypo}$.

A statistical simulation was performed to verify that an alarm threshold $G_{alarm}$ could be set that ranges from about hypoglycemic threshold $G_{hypo}$ and critical threshold $G_{crit}$ so that the occurrence of false positive and false negative errors could be at an acceptable level to the user. Inputs for the statistical simulation included about 10,000 patients using a CGM, a % CV of 3%, a % b ranging from about 6% to about 18%, a bgr ranging from about −0.05 mg/dL/min to about −5.0 mg/dL/min. Unless otherwise stated, the simulated glucose concentrations were synchronized to occur between $t_{lower}$ and $t_{upper}$. For this statistical simulation, the % cv and % b were incorporated into another term called mean average relative difference (MARD) that is indicative of overall accuracy and precision. MARD is defined in Equation 14.

$$MARD = \frac{1}{N} \times \sum_{i=1}^{N} \frac{|\hat{G}(t_i) - G(t_i)|}{G(t_i)} \quad \text{Eq. 14}$$

For the simulation, the resulting MARD ranged from about 5% to about 15% based on a % cv of 3% and a % b ranging from about 6% to about 18%.

Figure 4A:
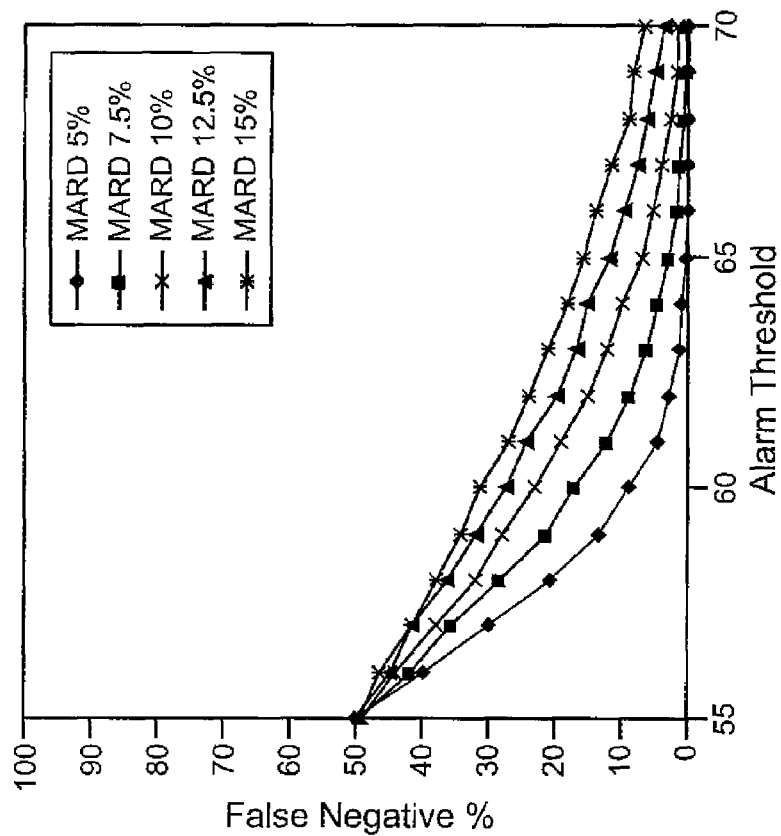
FIGS. 4A and 4B are graphs showing the incidence of false positive and false negative errors, respectively, when the alarm threshold is varied between 55 mg/dL and 70 mg/dL glucose concentration with a rate of change in glucose concentration per unit time of −0.5 mg/dL/min and a sampling rate of 1 sample per minute.
Figure 4B:
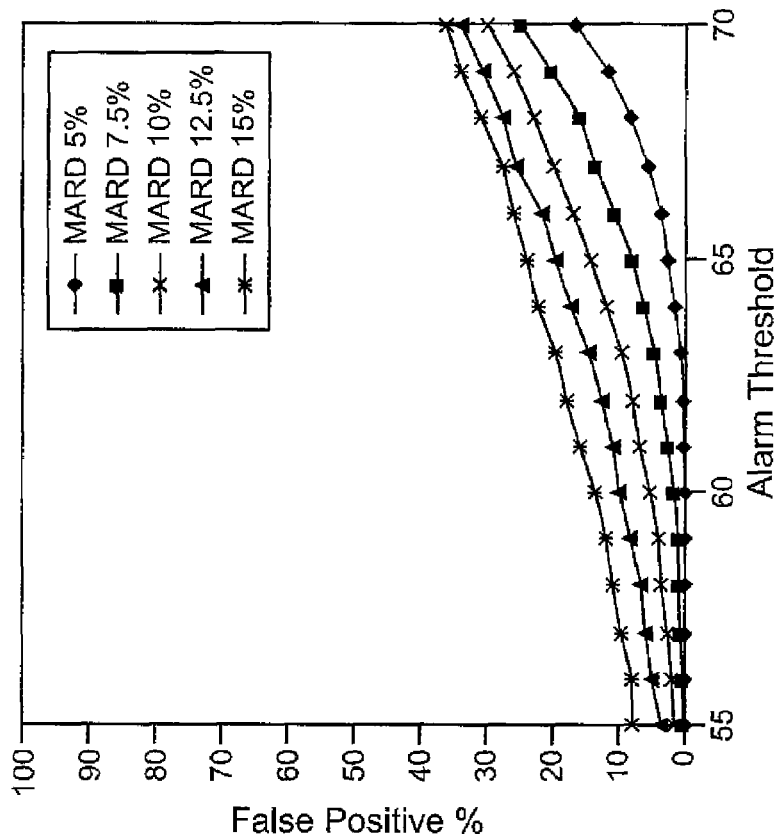
Figure 5B:
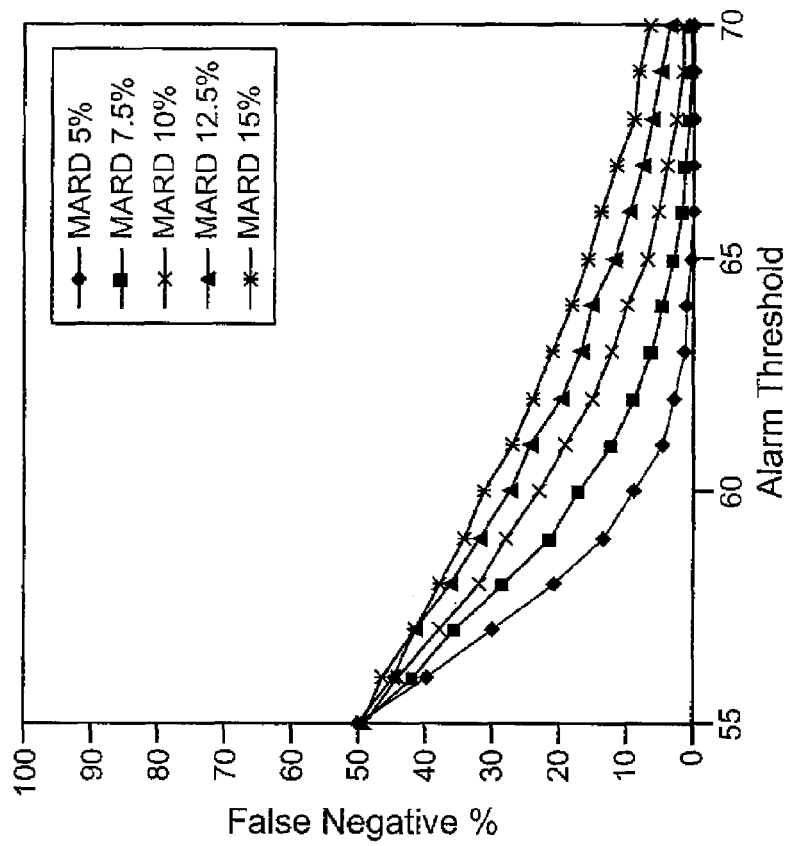
FIGS. 5A and 5B are graphs showing the incidence of false positive and false negative errors, respectively, when the alarm threshold is varied between 55 mg/dL and 70 mg/dL glucose concentration with a rate of change in glucose concentration per unit time of −0.5 mg/dL/min and a sampling rate of 0.1 samples per minute.
Figure 5A:
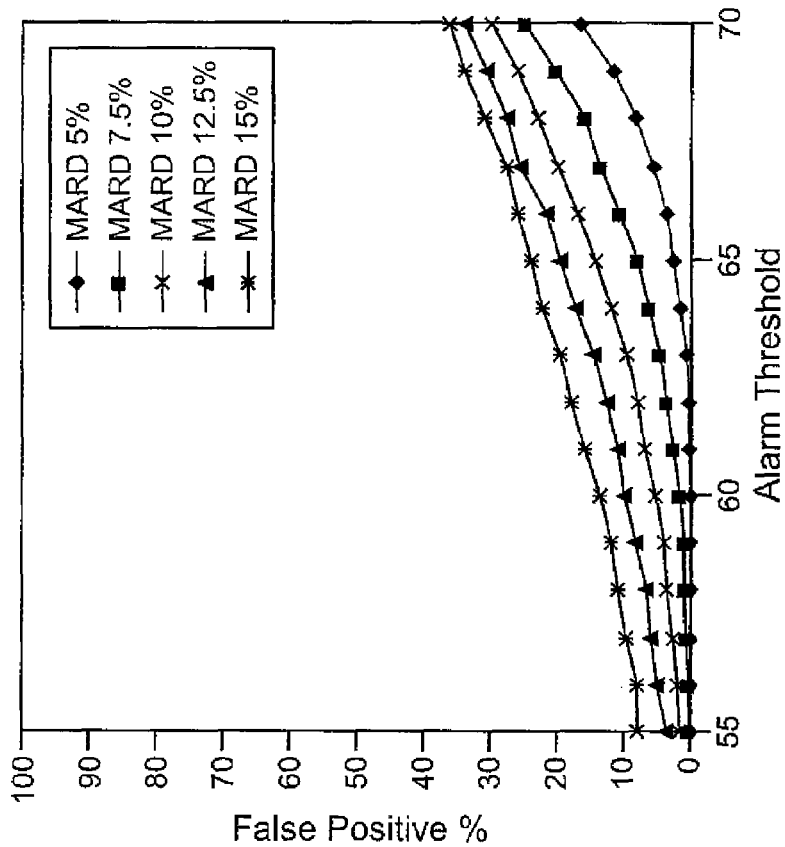

The following will describe a series of simulations using a wide range of bgr's (−5 mg/dL/min to −0.5 mg/dL/min) and a sampling rate that is in accord with the critical sampling rate in Equation 12. FIGS. 3A and 3B show the incidence of false positive errors and false negative errors, respectively, for a glucose rate of −1.0 mg/dL/min and a sampling rate of 0.2 samples/min. FIGS. 4A and 4B are similar to FIGS. 3A and 3B except that the glucose rate is −5.0 mg/dL/min and the sampling rate is 1 sample/min. FIGS. 5A and 5B are similar to FIGS. 3A and 3B except that the glucose rate is −0.5 mg/dL/min and the sampling rate is 0.1 samples/min. FIGS. 3 to 5 indicate that the false alarm incidence profiles are relatively constant over a wide range of bgr's because a critical sampling rate was used consistent with Equation 12.

FIGS. 3A, 4A, and 5A show that the incidence of false positives errors increased when the alarm threshold was close to the hypoglycemic threshold (70 mg/dL) and decreased when the alarm threshold was close to the critical threshold (55 mg/dL). FIGS. 3B, 4B, and 5B show that the incidence of false negative errors decreased when the alarm threshold was close to the hypoglycemic threshold (70 mg/dL) and increased when the alarm threshold was close to the critical threshold (55 mg/dL). For FIGS. 3 to 5, the overall false positive and false negative error rates increased with MARD.

The false error rates measured in FIGS. 3 to 5 were acquired using the critical sampling rate, as defined in Equation 12. In general, the false error rates in FIGS. 3 to 5 are very similar even though the sampling rates have a wide range of values from −0.5 mg/dL/min to −5.0 mg/dL/min, which supports the usefulness of the critical sampling rate, as defined in Equation 12. A relatively slow glucose rate of change of −0.5 mg/dL/min coupled with a relatively slow sampling rate of 0.1 samples/min achieved comparable error rates as the relatively fast sampling rate of 1 sample/minute coupled with a relatively fast glucose rate of change of −5.0 mg/dL/min, as illustrated in FIGS. 4 and 5. In summary, the results in FIGS. 3 to 5 verifies that faster sampling rates are needed for faster rates of change in glucose concentration per unit time and that slower sampling rates are needed for slower rates of change in glucose concentration per unit time for reducing both false negative and false positive errors.

Figure 7:
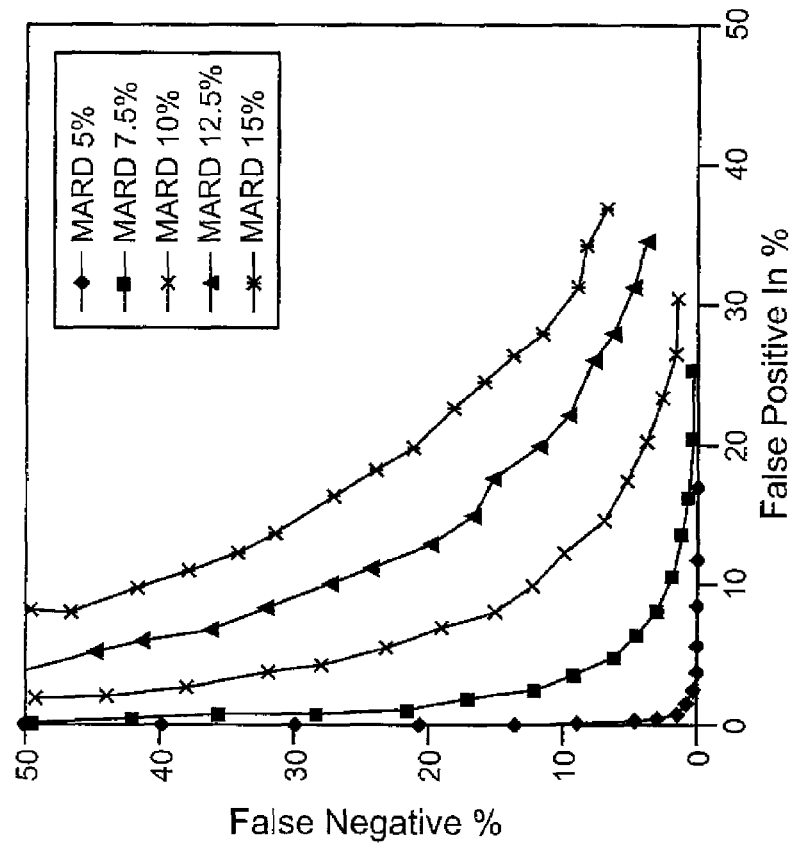
FIG. 7 is a graph illustrating the relationship between false positive and false negative errors based on the data of FIGS. 4A and 4B where the rate of change in glucose concentration per unit time is −5 mg/dL/min and the sampling rate is 1 samples per minute.
Figure 6:
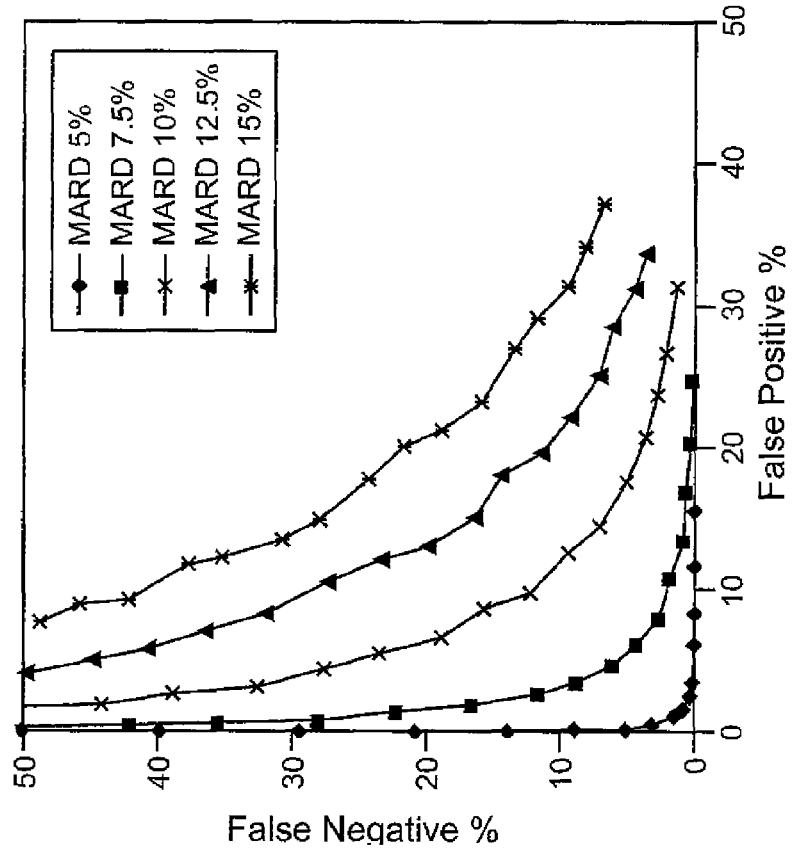
FIG. 6 is a graph illustrating the relationship between false positive and false negative errors based on the data of FIGS. 3A and 3B where the rate of change in glucose concentration per unit time is −1 mg/dL/min and the sampling rate is 0.2 samples per minute.

As another way to analyze a hypoglycemic alarm system, the false positive and false negative error rate of FIGS. 3A and 3B were combined into a single graph, as shown in FIG. 6. Similarly, FIGS. 4A and 4B were combined into a single graph, as shown in FIG. 7. Each data point in FIGS. 6 and 7 represents a particular alarm threshold and MARD. Both FIGS. 6 and 7 show that an improvement in false positive errors generally cause a decrease in false negative errors and vice versa. However, an optimum false positive and false negative error rate can be achieved by selecting an appropriate alarm threshold based on the circumstances. For example, a user that is in an intensive care unit could tolerate a higher false positive error rate, but could not tolerate a high false negative error rate because a delay in therapeutic action in intensive care can be very dangerous. In contrast, a person with type 2 diabetes having a mild form of the disease would likely not tolerate a relatively high false positive error rate because of the inconvenience, but could tolerate a higher false negative error rate because the potential for serious harm is much less likely to occur.

In an embodiment that is in accord with the present invention, a hypoglycemic alarm can have a false negative error of less than about 5% and a false positive error of less than about 10%. Based on FIGS. 6 and 7, a CGM would need a MARD of less than about 8% so that a hypoglycemic alarm can have a false negative error of less than about 5% and a false positive error of less than about 10%.

Figure 9:
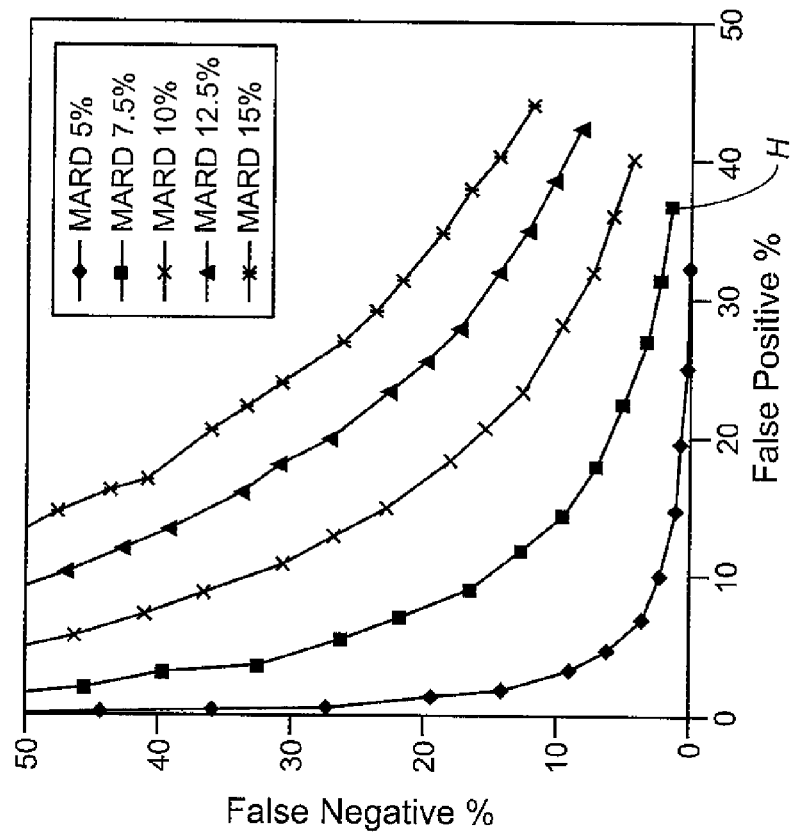
FIG. 9 is a graph illustrating the relationship between false positive and false negative errors for a CGM that has a sampling rate at about the critical sampling rate where the rate of change in glucose concentration per unit time is the same as FIG. 8.
Figure 8:
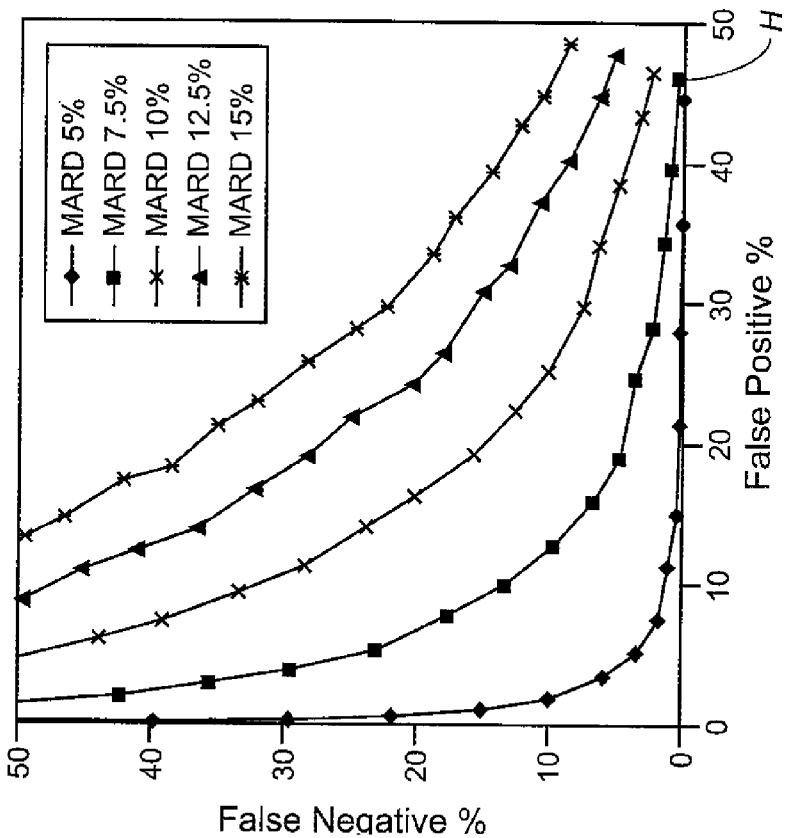
FIG. 8 is a graph illustrating the relationship between false positive and false negative errors for a CGM that has a sampling rate greater than the critical sampling rate where the rate of change in glucose concentration per unit time is −1 mg/dL/min.

FIG. 8 shows a false positive error rate and false negative error rate for a CGM that has a sampling rate greater than the critical sampling rate, which in this case was 0.4 samples/min for a rate of glucose change of −1 mg/dL/min. In contrast, FIG. 9 shows that decreasing the sample rate to about the critical sampling rate of 0.2 samples/min, where the rate of glucose change is the same as in FIG. 8, caused a decrease in the false positive error rate. Note that a data point "H" on both FIGS. 8 and 9, which has the same MARD and alarm threshold, clearly indicate a decrease in the false positive error rate when changing the sampling rate from being much greater than the critical sampling rate to being about the critical sampling rate. As a side note, FIGS. 8 and 9 do not have the glucose measurements synchronized to be within the target area. In summary, FIGS. 8 and 9 verified that using a sampling rate greater than the critical sampling rate, as defined in Equation 12, caused the false positive error rate to increase.

Figure 11:
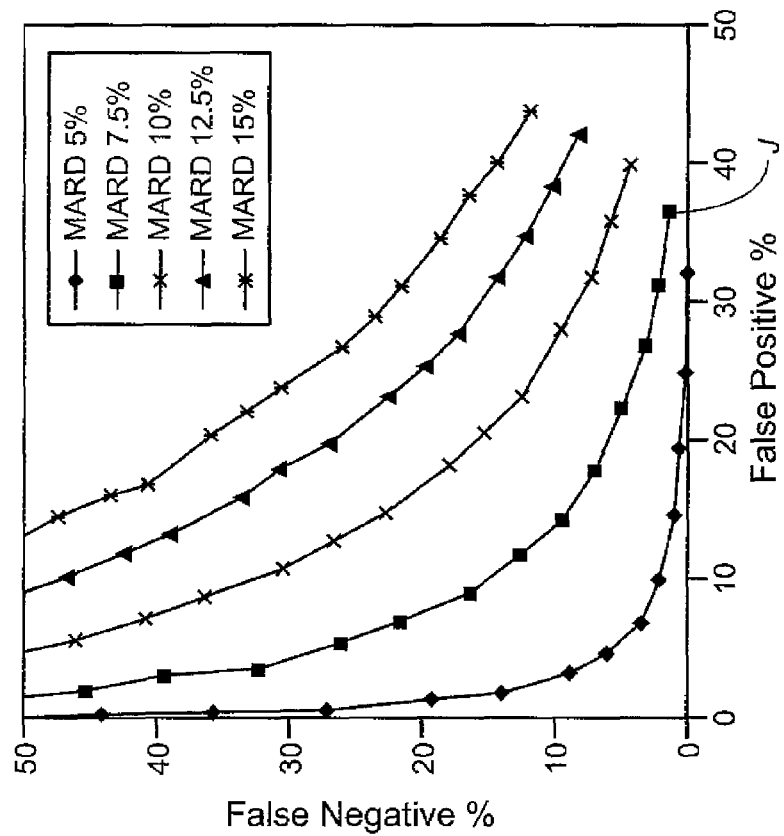
FIG. 11 is a graph illustrating the relationship between false positive and false negative errors for a CGM that has a sampling rate at about the critical sampling rate where the rate of change in glucose concentration per unit time is the same as FIG. 10.
Figure 10:
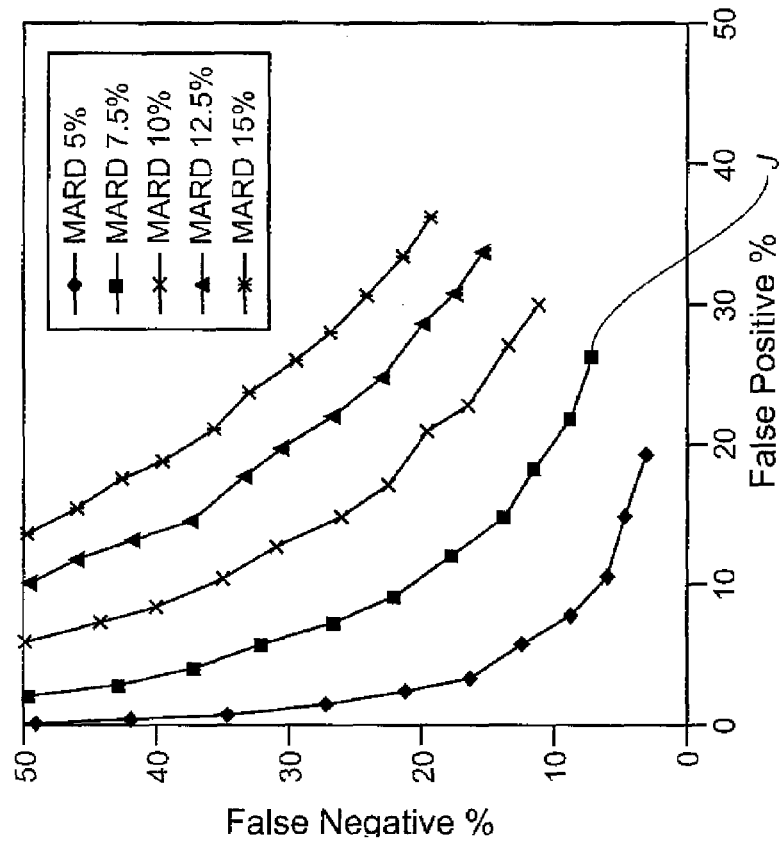
FIG. 10 is a graph illustrating the relationship between false positive and false negative errors for a CGM that has a sampling rate less than the critical sampling rate where the rate of change in glucose concentration per unit time is −1 mg/dL/min.

FIG. 10 shows a false positive error rate and false negative error rate for a CGM that has a sampling rate much less than the critical sampling rate, which in this case was 0.1 samples/min for a rate of glucose change of −1 mg/dL/min. In contrast, FIG. 11 shows that increasing the sample rate to about the critical sampling rate of 0.2 samples/min, where the rate of glucose change is the same as in FIG. 10, caused a decrease in the false negative error rate. Note that a data point "J" on both FIGS. 10 and 11, which has the same MARD and alarm threshold, clearly indicate a decrease in the false negative error rate when changing the sampling rate from being much less than the critical sampling rate to being about the critical sampling rate. As a side note, FIGS. 10 and 11 do not have the glucose measurements synchronized to be within the target area. In summary, FIGS. 10 and 11 verified that using a sampling rate less than the critical sampling rate, as defined in Equation 12, caused the false negative error rate to increase.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. While preferred embodiments of the present invention have been shown and described herein, it will be obvious to those skilled in the art that such embodiments are provided by way of example only. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. A method for establishing a critical sampling rate for a continuous glucose monitor having a continuous glucose sensor, processor, and memory, the method comprising the steps of:
    establishing with the processor and memory of the glucose monitor, a preferred number of measurements within a target zone, a predetermined critical threshold, and a predetermined hypoglycemic threshold, in which the target zone comprises a number of glucose measurements measured within a glucose concentration interval and within a time interval wherein said preferred number is about three;
    measuring with a continuous glucose sensor a plurality of glucose concentrations at a predetermined first sampling rate;
    calculating with the processor an actual rate of change in glucose concentration based on said plurality of glucose concentrations;
    modifying with the processor, said first sampling rate to a second sampling rate using a function based on said preferred number of measurements within a target zone, said predetermined critical threshold, said predetermined hypoglycemic threshold, and said actual rate of change in glucose concentration; and
    activating a hypoglycemic alarm to detect a hypoglycemic glucose concentration once said first sampling rate is modified to give a second sampling rate.

2. The method according to claim 1, wherein said step of modifying said first sampling rate to said second sampling rate comprises the steps of:
    multiplying said preferred number of measurements within a target zone with said actual rate of change in glucose concentration to give a product; and
    dividing said product by a difference between said predetermined critical threshold and said predetermined hypoglycemic threshold to give said second sampling rate.

3. The method according to claim 1, wherein said step of modifying said first sampling rate to said second sampling rate using said function based on an equation, said equation being $$\text{Second Sampling Rate} \geq \frac{TZ * bgr}{G_{crit} - G_{hypo}}$$

where $TZ$ is said preferred number of measurements within said target zone, $bgr$ is said actual rate of change in glucose concentration, $G_{crit}$ is said predetermined critical threshold, and $G_{hypo}$ is said predetermined hypoglycemic threshold.

4. The method according to claim 1 wherein said predetermined critical threshold is about 55 mg/dL and said predetermined hypoglycemic threshold is about 70 mg/dL.

5. The method according to claim 1 wherein said actual rate of change in glucose concentration ranges from about negative 5 milligram per deciliter per minute to about zero milligram per deciliter per minute.

6. The method according to claim 1 wherein said preferred number of measurements within said target zone is a number of glucose measurements within a glucose concentration interval and within a time interval,
    said glucose concentration interval is from about said predetermined critical threshold to about said predetermined hypoglycemic threshold, and
    said time interval is from a lower time value where said continuous glucose monitor is estimated to measure a glucose concentration at said predetermined hypoglycemic threshold to an upper time value where said continuous glucose monitor is estimated to measure a glucose concentration at said predetermined critical threshold.

* * * * *